United States Patent [19]

Shanaberger

[11] Patent Number: 5,628,204

[45] Date of Patent: May 13, 1997

[54] IN-HOME PERSONAL BLOOD STORAGE UNIT

[76] Inventor: Carrie L. Shanaberger, 5123 Amos Reeder Rd., Boonsboro, Md. 21713

[21] Appl. No.: 342,125

[22] Filed: Aug. 8, 1994

[51] Int. Cl.⁶ .......................... F25D 11/00; A61B 19/00
[52] U.S. Cl. ...................... 62/440; 62/62; 604/403
[58] Field of Search ................. 62/457.1, 457.9, 62/371, 440, 62; 604/403, 408, 410

[56] References Cited

U.S. PATENT DOCUMENTS

| | | | |
|---|---|---|---|
| 2,757,669 | 8/1956 | Gewecke et al. | 604/408 |
| 3,266,298 | 8/1966 | Whitehead et al. | 604/408 |
| 3,632,473 | 1/1972 | Belzer et al. | 62/306 |
| 4,326,526 | 4/1982 | Buck et al. | 604/410 X |
| 4,840,034 | 6/1989 | Liberman | 62/64 |
| 4,872,563 | 10/1989 | Warder et al. | 206/634 |
| 4,928,502 | 5/1990 | Kumada et al. | 62/440 |
| 4,959,062 | 9/1990 | Gellman | 604/403 |
| 5,103,651 | 4/1992 | Coelho et al. | 62/341 |
| 5,168,725 | 12/1992 | Margolin | 62/457.9 |
| 5,314,421 | 5/1994 | Leuenberger | 604/403 |

*Primary Examiner*—William Doerrler
*Attorney, Agent, or Firm*—Lowe, Price, LeBlanc & Becker

[57] ABSTRACT

The compact freezer including interior storage compartments, blood storage containers intended to fit into the compartments, which are labeled with identification tags. The instruction manual with the record-keeping chart greatly assists the entire process. The combination lock and the key lock are placed at the entry across from the alarm light; all of which assist with safety. The exterior file pocket is intended to store the manual and the chart.

23 Claims, 2 Drawing Sheets

5,628,204

IN-HOME PERSONAL BLOOD STORAGE UNIT

FIELD OF THE INVENTION

The present invention relates to a compact freezer unit for and method of storing one's blood at home. The freezer can include a combination lock and a key lock entry for a door for safekeeping of the blood; an alarm light indicating successful maintenance of storage of blood; interior divider compartments for organized multiple storage of small containers with the blood in them; the containers can include pint size containers with a blood storage bag that is labeled on its exterior for easy identification purposes. The unit and the storage containers can include an instruction manual and a record-keeping chart.

DESCRIPTION OF THE PRIOR ART

The American Red Cross is one organization which stores blood for the U.S.A. as a whole. Blood is donated by individuals at large storage facilities and is labeled by blood type and expiration dates. An individual donates blood to the Red Cross and, in a time of need, receives blood from the Red Cross. Most likely, the blood is from another person or several persons. Therefore, receiving blood by this method has risks of receiving a virus or deadly disease through blood transfusions.

Local hospitals will store, by refrigeration, an individual's own blood for up to 48 hours for his/her own use or use by the family of the individual by refrigeration. However, only one pint of blood can be drawn from an individual every 54 days.

SUMMARY OF THE INVENTION

It is an object of the invention to provide an individual with a personal unit to safely store his/her own blood and/or family's blood for up to ten years for use of one's own blood for self, family, or friends.

A further object of the invention is to provide a method of eliminating risks of disease through blood transfusions from large facilities.

BRIEF DESCRIPTION OF THE DRAWING

The present invention will be more fully understood by reference to the following detailed description when read in conjunction with the attached drawings, and wherein.

DETAILED DESCRIPTION OF THE DRAWINGS

Figure 1:
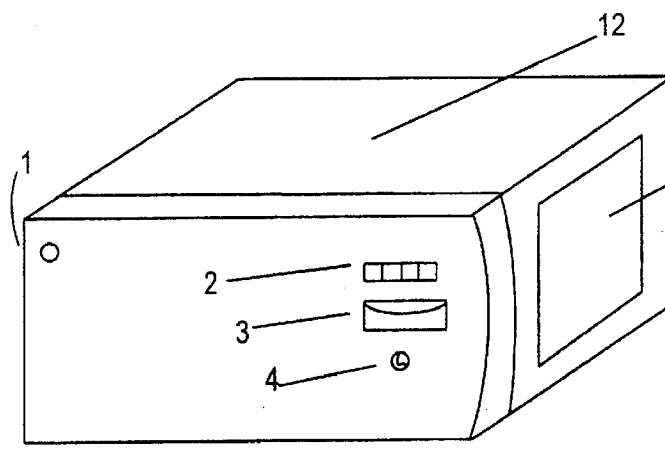
FIG. 1 is a front right perspective view of a preferred embodiment of the blood storage unit of the present invention.

As illustrated in FIG. 1, an in-home personal blood storage unit according to a preferred embodiment includes a compact freezer 12 having an alarm light 1, a door having a door handle 3 and a combination lock 2 and key lock 4 and a file compartment 5. File compartment 5 is attached on the exterior side of compact freezer 12. Interior frame 6, inside of compact freezer 12, includes storage compartments. A pint size blood storage bag 7 fits into the pint size container 8 to facilitate handling. For identification purposes, identification tag 9 is attached to storage container 8. Blood bag 7, placed inside container 8, has identification tag 9 attached on its exterior. Bag 7 and container 8 are then stored in compartment 6 which is inside compact freezer 12. The blood in bag 7 and container 8 is preferably stored at a temperature of no more than −65° in a freezer at a residence accessible to the individual whose blood is being stored. Detailed record-keeping chart 10, provided for optional use by the consumer, is stored in file compartment 5. Instruction manual 11 provides consumers with information about blood storage and blood usage and is an important part of the in-home personal blood storage unit.

Figure 2:
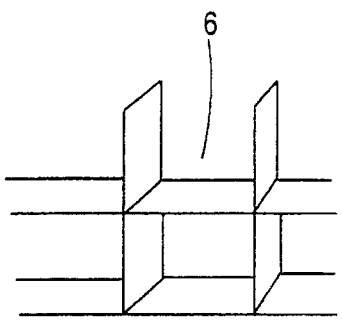
FIG. 2 is a perspective view of compartments inside the unit of FIG. 1.
Figure 3:
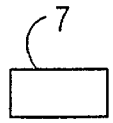
FIG. 3 is a front view of a storage bag for stored blood.
Figure 4:
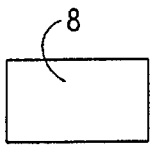
FIG. 4 is a front view of a pint-size container for receiving the bag of FIG. 3.
Figure 5:
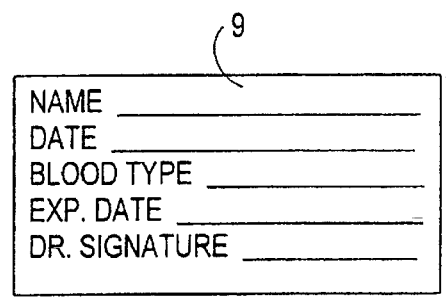
FIG. 5 is a front view of an identification tag to be placed in the container of FIG. 4.
Figure 6:
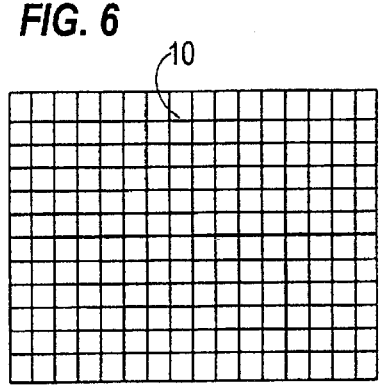
FIG. 6 is a front view of a record-keeping chart to be placed in the file compartment of the unit illustrated in FIG. 1.
Figure 7:
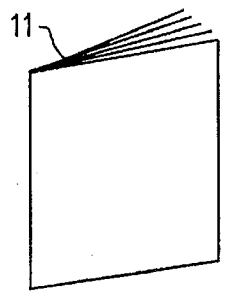
FIG. 7 is an instruction manual to be placed in the file compartment of the unit illustrated in FIG. 1.
Figure 8:
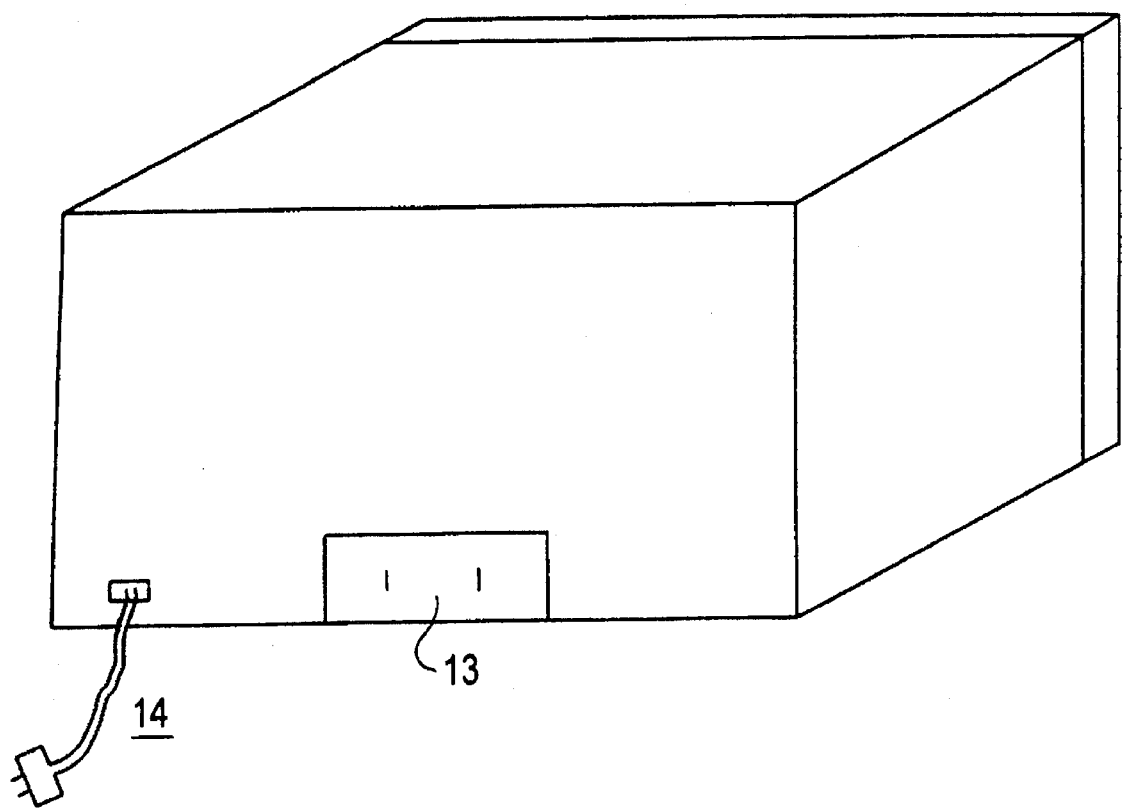
FIG. 8 is a right rear view of the unit illustrated in FIG. 1.

As illustrated in FIG. 2, the right back side of compact freezer 12 includes an electric cord connected to plug 14 for normally electrically powering the freezer by mains connected to the plug. Freezer 12 is optionally powered by a battery/generator unit connected to the freezer via outlet 13 during an electrical power outage.

While there has been described and illustrated one specific embodiment of the invention, it will be clear that variations in the details of the embodiment specifically illustrated and described may be made without departing from the true spirit and scope of the invention as defined in the appended claims.

I claim:

1. A method of storing an individual's own blood for later reuse for medicinal transfusion purposes comprising drawing a sufficient amount of blood from the individual to satisfy a medicinal transfusion purpose; storing the drawn blood in a frozen state at a temperature at which the blood can be reused, after thawing; the drawn blood being stored in a freezer at a residence accessible to the individual.

2. The method of claim 1 wherein the freezer is electrical and includes an electric mains supply connection and an auxiliary electric supply connection, and further comprising normally powering the freezer via the mains supply connection and powering the freezer via the auxiliary electric supply when there is a failure of the mains supply.

3. The method of claim 1 further including activating an alarm in response to temperature in the freezer increasing appreciably.

4. The method of claim 1 further including storing information about the stored blood.

5. The method of claim 4 wherein the information is stored on media located in a file pocket on the freezer.

6. The method of claim 4 further including storing an instruction manual in the file pocket on the freezer.

7. The method of claim 1 wherein the drawn blood is stored and maintained in a frozen state in relatively small containers in the freezer.

8. The method of claim 7 wherein the freezer includes a storage compartment where the containers are stored, the compartment including a door with a lock, normally maintaining the door in a locked condition and selectively opening the lock and the door when the containers are loaded into and removed from the compartment.

9. The method of claim 7 wherein the refrigerator includes interior storage compartments each having a size for receiving one of the containers, and placing one container in each compartment.

10. The method of claim 1 wherein the blood is drawn at a medical facility, and taking the drawn blood from the medical facility to the residence.

11. The method of claim 9 further including recording data concerning facts about the blood drawing on the container.

12. The method of claim 1 further including recording data concerning facts about the blood drawing.

13. Apparatus for enabling an individual to store his/her own drawn blood comprising plural relatively small containers where the drawn blood is located, each of the containers being of sufficient size to enable the blood to be used for medicinal transfusion purposes, the containers including identification indicia, and a freezer in which the blood in the containers is maintained in a frozen state, the freezer being located at a residence accessible to the person from whom the blood was drawn.

14. The apparatus of claim 13 wherein the containers are able to hold approximately one pint of blood.

15. The apparatus of claim 13 further including a record-keeping medium storing data assisting in providing information about testing of the blood of the individual and future scheduling of drawing blood of the individual.

16. The apparatus of claim 15 wherein the medium is on a wall of the freezer.

17. The apparatus of claim 13 wherein the freezer includes a door with a lock.

18. The apparatus of claim 17 wherein the lock is a key lock.

19. The apparatus of claim 17 wherein the lock is a combination lock.

20. The apparatus of claim 13 wherein the freezer includes an alarm for indicating excessive temperature in the freezer.

21. The apparatus of claim 13 wherein the freezer is electrical and includes an electric mains supply connection and an auxiliary electric supply connection, the freezer being normally powered via the mains connection and being powered via the auxiliary connection when there is a failure of the mains supply.

22. The method of claim 1 wherein the blood is stored in the freezer at the residence at a temperature no more than −65° F.

23. The method of claim 1 further comprising the step of thawing the stored blood and administering it for medicinal purposes to the individual or a person known to the individual.

* * * * *